(12) United States Patent
Nakai et al.

(10) Patent No.: US 10,219,775 B2
(45) Date of Patent: Mar. 5, 2019

(54) PHOTON-COUNTING X-RAY CT APPARATUS AND IMAGE PROCESSING APPARATUS

(71) Applicant: TOSHIBA MEDICAL SYSTEMS CORPORATION, Otawara-shi (JP)

(72) Inventors: Hiroaki Nakai, Nasushiobara (JP); Mikihito Hayashi, Otawara (JP); Tooru Kato, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 175 days.

(21) Appl. No.: 15/336,222

(22) Filed: Oct. 27, 2016

(65) Prior Publication Data
US 2017/0119340 A1  May 4, 2017

(30) Foreign Application Priority Data

Nov. 2, 2015 (JP) .................................. 2015-216028
Sep. 14, 2016 (JP) .................................. 2016-179659

(51) Int. Cl.
*A61B 6/00* (2006.01)
*A61B 6/03* (2006.01)

(52) U.S. Cl.
CPC .............. *A61B 6/585* (2013.01); *A61B 6/032* (2013.01); *A61B 6/4241* (2013.01); *A61B 6/461* (2013.01); *A61B 6/54* (2013.01)

(58) Field of Classification Search
None
See application file for complete search history.

(56) References Cited

U.S. PATENT DOCUMENTS

| | | | |
|---|---|---|---|
| 7,372,934 B2 | 5/2008 | De Man et al. | |
| 2014/0105370 A1* | 4/2014 | Yamakawa | A61B 6/025 378/207 |
| 2014/0328465 A1 | 11/2014 | Herrmann | |

FOREIGN PATENT DOCUMENTS

| | | |
|---|---|---|
| JP | 2000-23965 | 1/2000 |
| JP | 2007-167663 | 7/2007 |
| JP | 2015-505968 | 2/2015 |

* cited by examiner

*Primary Examiner* — Hoon K Song
(74) *Attorney, Agent, or Firm* — Oblon, McClelland, Maier & Neustadt, L.L.P.

(57) ABSTRACT

A photon-counting X-ray computed tomography (CT) apparatus according to an embodiment includes an X-ray tube, a detector, a photon counting circuitry, a correcting circuitry, and a calculating circuitry. The X-ray tube irradiates a subject with X-rays. The detector includes a plurality of detection elements that detect photons of X-rays incident on the detection elements. The photon counting circuitry counts the count of X-ray photons for each energy bin set in an X-ray energy distribution, for each position of the X-ray tube, and for each of the detection elements. The correcting circuitry corrects the count of the X-ray photons counted by the photon counting circuitry, based on a detection characteristic, of the detection elements. The calculating circuitry calculates the reliability of a pixel in a reconstruction image, based on the correction.

10 Claims, 6 Drawing Sheets

PHOTON-COUNTING X-RAY CT APPARATUS AND IMAGE PROCESSING APPARATUS

CROSS-REFERENCE TO RELATED APPLICATIONS

This application is based upon and claims the benefit of priority from Japanese Patent Application No. 2015-216028, filed on Nov. 2, 2015, and Japanese Patent Application No. 2016-179659 filed on Sep. 14, 2016, the entire contents of which are incorporated herein by reference.

FIELD

Embodiments described herein relate generally to photon-counting X-ray computed tomography (CT) apparatus and an image processing apparatus.

BACKGROUND

Photon-counting X-ray CT apparatuses detect the photon count and the energy level of the X-rays incident on each of the detection elements, generates a CT image for each of the different energy levels, and decomposes substances and estimates the substance densities. This is also referred to as multi-energy reconstruction.

When a large number of photons become incident on the detection elements, however, such a photon-counting X-ray CT apparatus sometimes falls incapable of decomposing the substances or estimating the substance densities appropriately. This is because the waveforms generated by the individual photons overlap one another, due to the response time of the detection elements, and, as a result, a plurality of photons are counted as one photon. This phenomenon is referred to as pulse pile-up.

DETAILED DESCRIPTION

A photon-counting X-ray CT apparatus according to an embodiment includes an X-ray tube, a detector, photon counting circuitry, correcting circuitry, and calculating circuitry. The X-ray tube irradiates a subject with X-rays. The detector includes a plurality of detection elements detecting the photons of the X-rays being incident on the detection elements. The photon counting circuitry counts a photon count of X-rays for each energy bin set in an X-ray energy distribution, for each position of the X-ray tube, and for each of the detection elements. The correcting circuitry corrects the X-ray photon count counted by the photon counting circuitry based on detection characteristics of the corresponding detection element. The calculating circuitry calculates the reliability of a pixel in the reconstruction image based on the correction.

A photon-counting X-ray CT apparatus according to an embodiment will now be explained with reference to the accompanying drawings. In the embodiment described below, redundant explanations will be omitted as appropriate.

Embodiment

Figure 1:
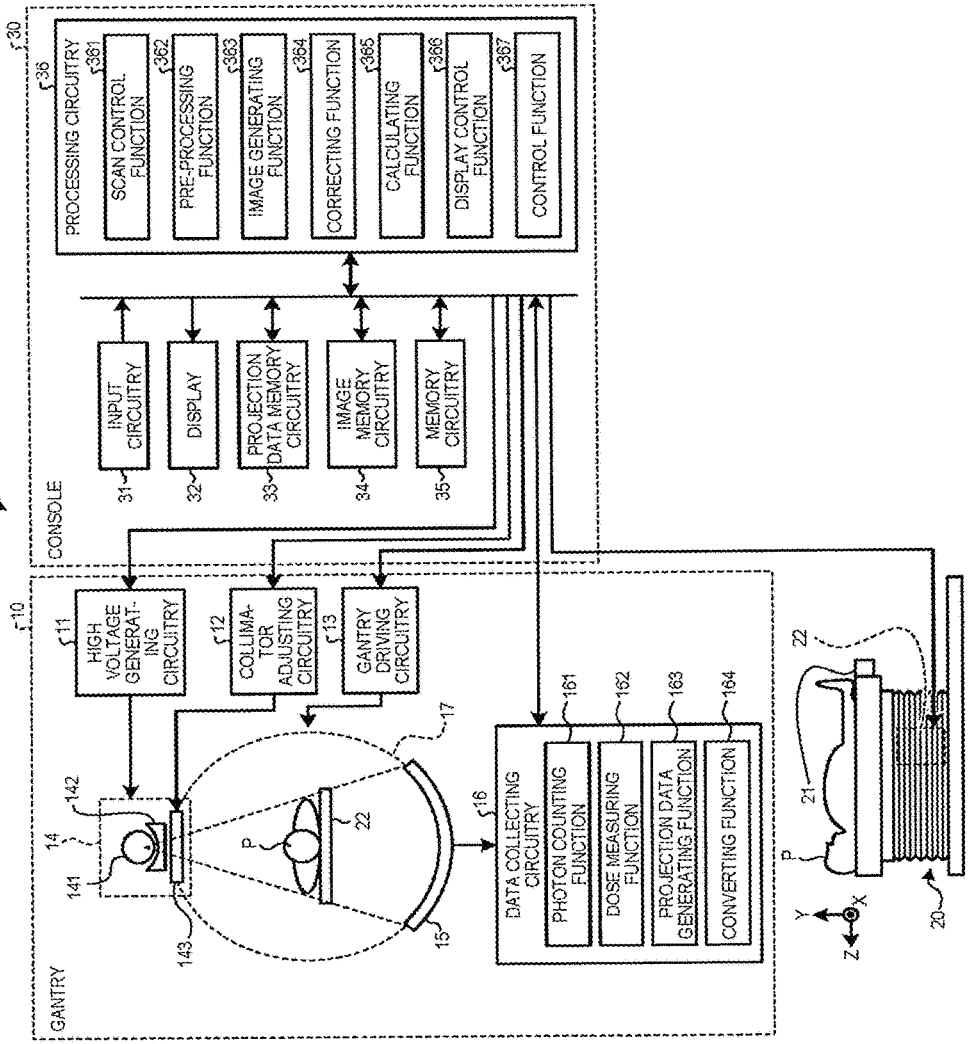
FIG. 1 is a schematic illustrating an exemplary configuration of a photon-counting X-ray CT apparatus according to an embodiment.

A configuration of a photon-counting X-ray CT apparatus 1 according to the embodiment will now be explained with reference to FIG. 1. FIG. 1 is a schematic illustrating an exemplary configuration of the photon-counting X-ray CT apparatus according to the embodiment. The photon-counting X-ray CT apparatus 1 includes, as illustrated in FIG. 1, a gantry 10, a couch 20, and a console 30. The configuration of the photon-counting X-ray CT apparatus 1 is, however, not limited to the configuration described below.

The gantry 10 includes high voltage generating circuitry 11, collimator adjusting circuitry 12, gantry driving circuitry 13, an X-ray radiation device 14, a detector 15, data collecting circuitry 16, and a rotating frame 17.

The high voltage generating circuitry 11 supplies a tube voltage to an X-ray tube 141 described later. The high voltage generating circuitry 11 implements this function by reading a computer program stored in memory circuitry 35 described later an 3 executing the computer program.

The collimator adjusting circuitry 12 adjusts the aperture degree and the position of a collimator 143 described later. Through this adjustment, the collimat adjusting circuitry 12 adjusts the irradiation range of the X-rays with which a subject P is irradiated by the X-ray the 141. The collimator adjusting circuitry 12 implements this function by reading a computer program stored in the memory circuitry 35 described later and executing the computer program.

The gantry driving circuitry 13 drives the rotating frame 17 in rotation. Through this operation, the gantry driving circuitry 13 causes the X-ray radiation device 14 and the detector 15 to revolve along a circular trajectory about the subject P. The gantry driving circuitry 13 implements this function by reading a computer program stored in the memory circuitry 35 described later and executing the computer program.

The X-ray radiation device 14 includes the X-ray tube 141, a wedge 142, and the collimator 143. The X-ray tube 141 irradiates the subject P with X-rays. The X-ray tube 141 generates beam-like X-rays using the tube voltage supplied by the high voltage generating circuitry 11. The beam-like X-rays are also referred to as cone beams. The wedge 142 is an X-ray filter for adjusting the dose of the X-rays output from the X-ray tube 141. The collimator 143 is a slit for adjusting the range irradiated with the X-rays. The aperture degree and the position of the collimator 143 are adjusted by the collimator adjusting circuitry 12. Through the adjustment of the aperture degree of the collimator 143, the fan angle and the cone angle of the cone beam, for example, are adjusted.

The detector 15 includes a plurality of detection elements detecting the photons of the X-rays being incident on the detection elements. The detection elements are arranged regularly along a first direction and a second direction intersecting with the first direction. For example, the first direction corresponds to a channel direction, the second direction corresponds to a slice direction. In this example, the channel direction corresponds to the circumferential direction of the rotating frame 17, and the slice direction corresponds to a I direction. This detector is referred a multi-row detector.

Each of the detection elements includes a scintillator, a photodiode, photon-counting detecting circuitry, and integration detecting circuitry. The detector with detection elements each having a scintillator and a photodiode is referred to as a solid-state detector. The input terminal of the photon-counting detecting circuitry is connected to the output terminal of the photodiode. The output terminal of the photon-counting detecting circuitry is connected to the input terminal of the data collecting circuitry 16. The input terminal of the integration detecting circuitry is connected to the output terminal of the photodiode. The output terminal of the integration detecting circuitry is also connected to the input terminal of the data collecting circuitry 16.

The detection elements convert the incident X-ray photons into a response waveform or a voltage pulse in the manner described below. The scintillator in the detection elements converts the incident X-ray photons into light, and the photodiode in th detection elements then converts the light into an electric charge. This electric charge is output to the photon-counting detecting circuitry and the integration detecting circuitry. The photon-counting detecting circuitry outputs a response waveform to the data collecting circuitry 16. The response waveform is time-sequence data of voltages generated by the photons incident on each of the detection elements, at the corresponding position of the X-ray tube 141. The integration detecting circuitry outputs a voltage pulse to the data collecting circuitry 16. The voltage pulse is the sum of the voltages generated by the entire photons incident on the detection elements, at the respective positions of the X-ray tube 141.

The detector 15 may also be a direct-conversion detector. The direct-conversion detector is a detector that directly converts the X-rays being incident on the detection element into an electric charge. The direct-conversion detector outputs this electric charge as a result of at least one of the movement of the electrons generated by the incident X-rays in a direction toward a collecting electrode at a positive potential and the movement of the positive holes generated by the incident X-rays in a direction toward the collecting electrode at a negative potential.

The data collecting circuitry 16 has a photon counting function 161, a dose measuring function 162, a projection data generating function 163, and a converting function 164. These functions will be described later in detail. The data collecting circuitry 16 is implemented by a processor, for example. The data collecting circuitry 16 is also referred to as a data acquisition system (DAS).

The rotating frame 17 is a ring-shaped frame supporting the X-ray radiation device 14 and the detector 15, with the subject P interposed therebetween. The rotating frame 17 is driven by the gantry driving circuitry 13, and is rotated at a high speed along a circular trajectory about the subject P.

The couch 20 includes a couchtop 21 and couch driving circuitry 22. The couchtop 21 is a plate-like member which the subject P can be laid. The couch driving circuitry 22 moves the subject P inside an image capturing opening of the gantry 10, by causing the couchtop 21 on which the subject P is laid to move in the body axis direction. The couch driving circuitry 22 implements this function by reading a computer program stored in the memory circuitry described later and executing the computer program.

The console 30 includes input circuitry 31, a display 32, projection data memory circuitry 33, image memory circuitry 34, memory circuitry 35, and processing circuitry 36.

The input circuitry 31 is used by a user who is entering instructions and settings. The input circuitry 31 is included in a mouse and a keyboard, for example. The input circuitry 31 forwards the instructions and the settings entered by the user to the processing circuitry 36. The input circuitry 31 is implemented by a processor, for example.

The display 32 is a monitor referred to by a user. Examples of the display 32 include a liquid crystal display and an organic electroluminescence (EL) display. The display 32 receives an instruction for displaying a reconstruction image or a graphical user interface (GUI) used by a user when the user enters instructions or settings, for example, from the processing circuitry 36. The display 32 displays the reconstruction image, the GUI, and the like based on such an instruction. Examples of the reconstruction image include a morphological image, a substance decomposing image, an electron density image, an effective atomic number image, and a monochromatic X-ray image. Morphological images are generated by reconstructing integral projection data. Morphological images may also be generated by reconstructing photon-counting projection data representing the sum of X-ray photon counts across a plurality of energy bins. The photon-counting X-ray CT apparatus 1 can omit the display 32.

The projection data memory circuitry 33 stores therein raw data generated by a pre-processing function 362, which will be described later. The image memory circuitry 34 stores therein a reconstruction image generated by an image generating function 363, which will be described later.

The memory circuitry 35 stores therein computer programs for causing the high voltage generating circuitry 11, the collimator adjusting circuitry 12, the gantry driving circuitry 13, and the data collecting circuitry 16 to implement the functions described above. The memory circuitry 35 also stores therein a computer program for causing the couch driving circuitry 22 to implement the functions described above. The memory circuitry 35 also stores therein a computer program for causing the processing circuitry 36 to implement the functions described later.

The projection data memory circuitry 33, the image memory circuitry 34, and the memory circuitry 35 include a storage medium from which information stored in these circuitry can be read with a computer. An example of the storage medium is a hard disk.

The processing circuitry 36 has a scan control function 361, a pre-processing function 362, an image generating function 363, a correcting function 364, a calculating function 365, a display control function 366, and a control function 367. The correcting function 364 corrects an X-ray photon count counted by the photon counting function 161 based on the detection characteristics of a detection element. The image generating function 363 generates a reconstruction image based on the result corrected by the correcting function 364. The calculating function 365 calculates the reliability of pixels in the reconstruction image based on the result corrected by the correcting function 364. These functions will be described later in detail. The processing circuitry 36 is implemented by a processor, for example.

Figure 2:
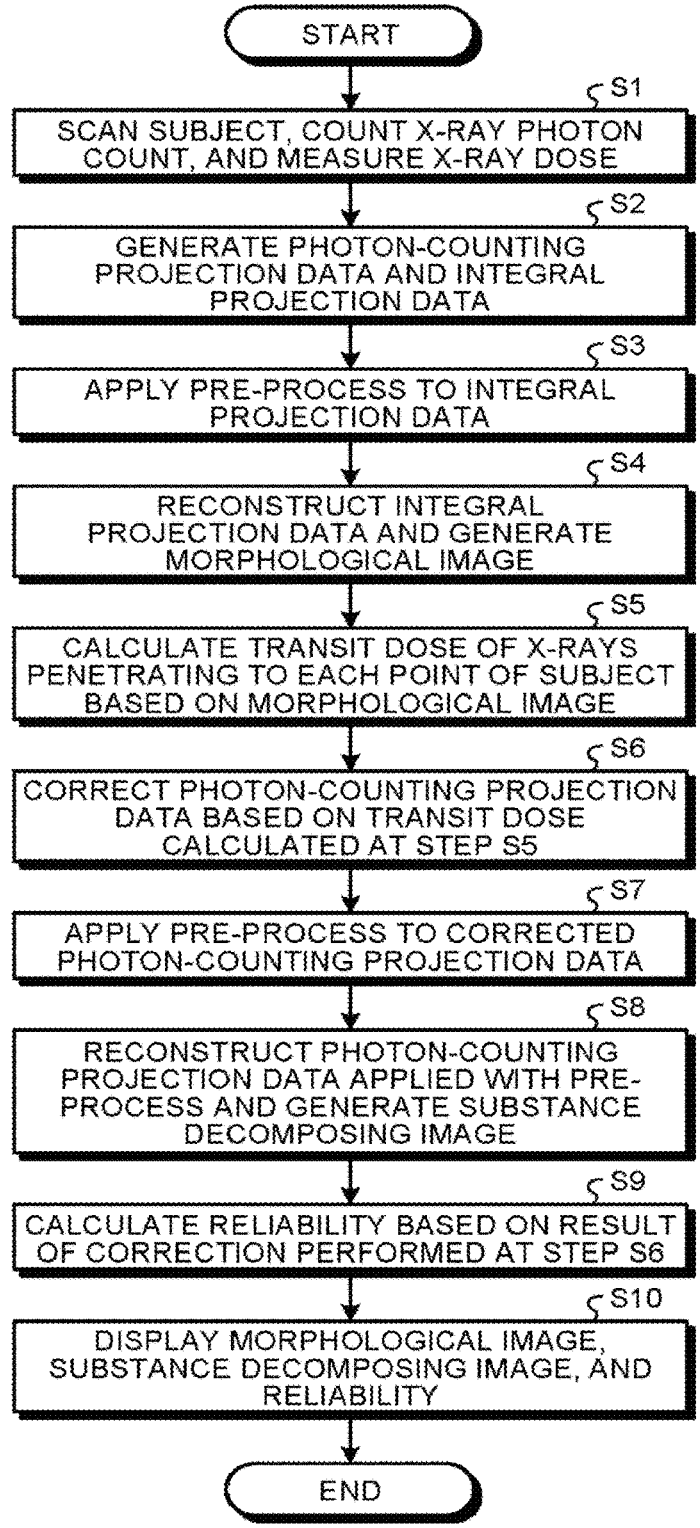
FIG. 2 is a flowchart illustrating an exemplary process performed by the photon-counting X-ray CT apparatus according to the embodiment.

An exemplary process performed by the photon-counting X-ray CT apparatus 1 according to the embodiment will now be explained with reference to FIGS. 2 to 8. FIG. 2 is a flowchart illustrating the exemplary process performed by the photon-counting X-ray CT apparatus according to the embodiment. References to FIGS. 3 to 8 are made as appropriate, in explaining the exemplary process performed by the photon-counting X-ray CT apparatus 1.

The processing circuitry 36 scans the subject, counts the X-ray photon count, and measures the X-ray dose (Step S1), as illustrated in FIG. 2. An example of the process at Step S1 is as described below.

The processing circuitry 36 reads a computer program corresponding to the scan control function 361 from the memory circuitry 35 and executes the computer program. The scan control function 361 is a function for controlling and causing the photon-counting X-ray CT apparatus 1 to execute scanning. The processing circuitry o controls the photon-counting X-ray CT apparatus 1 in the manner described below, for example, by executing the scan control function 361.

The processing circuitry 36 controls the couch driving circuitry 22 to move the subject P into the image capturing opening of the gantry 10. The processing circuitry 36 executes scanning of the subject P by controlling the gantry driving circuitry 13. Specifically, the processing circuitry 36 controls the high voltage generating circuitry 11 to supply the tube voltage to the X-ray tube 141. The processing circuitry 36 controls the collimator adjusting circuitry 12 to adjust the aperture degree and the position of collimator 143. The processing circuitry 36 also controls the gantry driving circuitry 13 to rotate the rotating frame 17.

Exemplary types of scan executed by the photon-counting X-ray CT apparatus 1 include conventional scan, helical scan, and step-and-shoot. The conventional scan is a technique for scanning the subject P laid on the couchtop 1, with the position of the subject P fixed. The helical scan is a technique for scanning the subject P laid on the couchtop 21 while moving the subject P along the body axis direction. The step-and-shoot is a technique for performing the conventional scan across a plurality of scan sections by moving the position of the subject P laid on the couchtop 21 at a certain interval.

The processing circuitry 36 controls the data collecting circuitry 16 to count the X-ray photon count and to measure the X-ray dose. The data collecting circuitry 16 performs the process described below, for example.

The data collecting circuit y 16 reads a computer program corresponding to th photon counting function 161 from the memory circuitry 35 and executes the computer program. The photon counting function 161 counts the number of events at which the response waveform output from the photon-counting detecting circuitry keeps exceeding a predetermined threshold. Through this operation, the photon counting function 161 counts the X-ray photon count being incident on the detection element. The photon counting function 161 also calculates the wave height and the waveform area of the response waveform output from the detection element. Through this operation, the photon counting function 161 calculates the energy of the X-ray photon incident on the detection element. Therefore, the photon counting function 161 can count the X-ray photon count for each energy bin set in the X-ray energy distribution, each position of the X-ray tube 141, and for each of the detection elements.

The data collecting circuitry 16 reads a computer program corresponding to the dose measuring function 162 the memory circuitry 3 and executes the computer program. The dose measuring function 162 calculates an integral of the voltage pulses output from the integration detecting circuitry. Through this operation, the dose measuring function 162 measures the dose of X-rays incident on the detection element.

The processing circuitry 36 then generates photon-counting projection data and integral projection data, as illustrated in FIG. 2 (Step S2). An example of the process at Step S2 is as described below.

The data collecting circuitry 16 reads a computer program corresponding to th projection data generating function 163 from the memory circuitry 35 and executes the computer program. The projection data generating function 163 is a function for generating projection data based on the response waveform or the voltage pulse output from the detection element. An example of the projection data is a sinogram. The sinogram is a data consisting of an arrangement of the photon counts or the doses of the X-rays having become incident on the respective detection elements, at each position of the X-ray tube 141. The position of the. X-ray tube 141 is referred to as a view. In other words, the sinogram is data in which X-ray photon counts or X-ray doses are plotted in a Cartesian coordinate system with its axes representing a view direction and a channel direction, respectively. The projection data generating function 163 generates a sinogram in unit of row in the slice direction, for example.

The projection data generating function 163 generates the photon-counting projection data based on the X-ray photon counts counted by the photon counting function 161. The luminance at each pixel in the photon-counting projection data represents an X-ray photon count counted for each energy bin set in the X-ray energy distribution, for each position of the X-ray tube, and for each of the detection elements. The projection data generating function 163 generates integral projection data based on the X-ray doses measured by the dose measuring function 162. The luminance at each pixel in the integral projection data represents the dose of X-rays incident on the corresponding detection element, at each position of the X-ray tube 141.

The data collecting circuitry 16 may read a computer program corresponding to th converting function 164 from the memory circuitry 35 and execute the computer program before reading the computer program corresponding to the projection data generating function 163 from the memory circuitry 35 and executing the computer program. The converting function 164 is a function for calculating the attenuation coefficient of the X-rays penetrating through the subject P, from the X-ray photon counts counted by th photon counting function 161, or for calculating a projection length of the X-rays penetrating through the subject P from the X-ray photon counts counted by the photon counting function 161.

In such a case, the projection data generating function 163 generates photon-counting projection data representing the attenuation coefficient of the X-rays penetrating through the subject P, or the projection length of the X-rays through the subject P, based on the X-ray photon count counted by the photon counting function 161. Denoting the energy distribution (energy spectrum) of the photon counts counted at some coordinates of some photon-counting projection data as I, denoting the energy spectrum of X-rays emitted from the X-ray tube 141 and before being incident on the subject P as $I_0$, denoting the energy as E, and the attenuation coefficient of the K-rays being incident on the coordinates for the subject P as μ, Equation (1) is established.

$$\log(I(E)/I_0(E)) = \int -\mu(E) dL \quad (1)$$

In the equation, L denotes the projection length through the subject P. If the subject P consists of one substance, and the attenuation coefficient μ is known, Equation (1) can be converted into a projection length using Equation (2).

$$-\log(I(E)/I_0(E)) = \mu(E) \cdot L \quad (2)$$

The subject P is, however, usually patient, and therefore consists of a plurality of substances. Furthermore, with the contrast imaging, the X-ray CT apparatus 1 is required to generate a reconstruction image decomposing a contrast agent. Therefore, for example, assuming that basis substances are two (two of muscle tissues, bones, and the contrast agent, for example), Equation (2) can be represented as Equation (3).

$$-\log(I(E)/I_0(E)) = \mu_1(E) \cdot L_1 + \mu_2(E) \cdot L_2 \quad (3)$$

The converting function 164 calculates projection lengths $L_1$ and $L_2$ for the two respective substances. The projection lengths $L_1$ and $L_2$ for the two respective substances are calculated, with respect to the energy E, in plurality. Therefore, the converting function 164 acquires the projection lengths $L_1$ and $L_2$ by statistically solving the equation. The number of basis substances is not limited to a particular number.

When projection length $L(=L_1+L_2)$ is already acquired from the integral projection data, the converting function 164 can calculate the attenuation coefficient. When there is some assumption related to the basis substances, the converting function 164 can also convert the mass attenuation coefficients of the basis substances into substance densities.

By using the projection length or the attenuation coefficient calculated in the manner described above as a luminance of the corresponding pixel in the projection data, the projection data generating function 163 can generate photon-counting projection data representing the projection length or the attenuation coefficient.

The processing circuitry 36 then applies a pre-process to the integral projection data, as illustrated in FIG. 2 (Step S3). An example of the process at Step S3 is as described below.

The processing circuitry 36 reads a computer program corresponding to the pre-processing function 362 from the memory circuitry 35 and executes the computer program. The pre-processing function 362 is a function for correcting the projection data generated by the data collecting circuitry 16. Examples of the correction include logarithmic transformation, offset correction, sensitivity correction, beam hardening correction, and scattered-ray correction. The integral projection data corrected by the pre-processing function 362 is stored in the projection data memory circuitry 33. The integral projection data corrected by the pre-processing function 362 is also referred to as raw data.

The processing circuitry 36 reconstructs the integral projection data, and generates a morphological image, as illustrated in FIG. 2 (Step S4). An example of the process at Step S4 is as described below.

The processing circuitry 36 reads a computer program corresponding to the image generating function 363 from the memory circuitry 35 and executes the computer program. The image generating function 363 includes a function for generating a morphological image by reconstructing the integral projection data stored in the projection data memory circuitry 33. Examples of the reconstruction method include back projection and iterative reconstruction. An example of the back projection includes filtered back projection (FBP). The morphological image generated by the image generating function 363 is stored in the image memory circuitry 34. The morphological image generated at Step 34 may be either a two-dimensional morphological image or a three-dimensional morphological image.

The processing circuitry 36 calculates the transit dose of the X-rays penetrating to each point of the subject, based on morphological image (Step S5). An example of the process at Step S5 is as described below.

The processing circuitry 36 reads a computer program corresponding to tho correcting function 364 from the memory circuitry 35 and executes the computer program. For each of the point corresponding to points of the subject P in the morphological image generated at Step S4, the correcting function 364 calculates the transit dose of the X-rays penetrating to the point, and becoming incident on the detection element. Specifically, the correcting function 364 calculates th transit dose of the X-rays penetrating to each of the points, corresponding to points of the subject P, of the morphological image generated at Step S4, based on a calculation of a line integral of CT values over a line passing through the point. The correcting function 364 may also calculate the transit dose of th X-rays penetrating to each point of the subject P based on L luminance at the corresponding pixel in the integral projection data. The X-ray transit dose calculated at Step S5 is dependent on the incident angle of th X-rays. The behavior of the X-ray transit dose calculated at Step CS with respect to the X-ray incident angle will now be explained with reference to FIGS. 3, 4, and 5.

Figure 3:
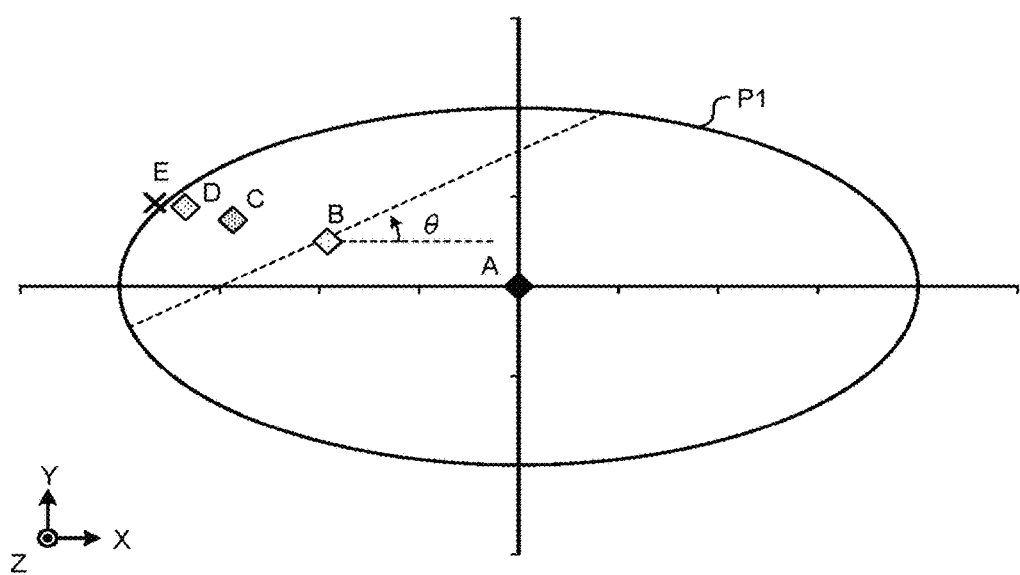
FIG. 3 is a schematic illustrating an exemplary subject having a uniform linear attenuation coefficient of X-rays.

FIG. 3 is a schematic illustrating an exemplary subject having a uniform linear attenuation coefficient of X-rays. Used in explaining the exemplary process performed by the photon-counting X-ray CT apparatus 1 is an example in which a subject P1 illustrated in FIG. 3 is scanned. The subject P1 is an elliptic cylinder with a central axis extending in parallel with the Z-axis, and with a bottom surface extending in parallel with the XY plane. The subject P1 also has a uniform linear attenuation coefficient of X-rays.

Figure 4:
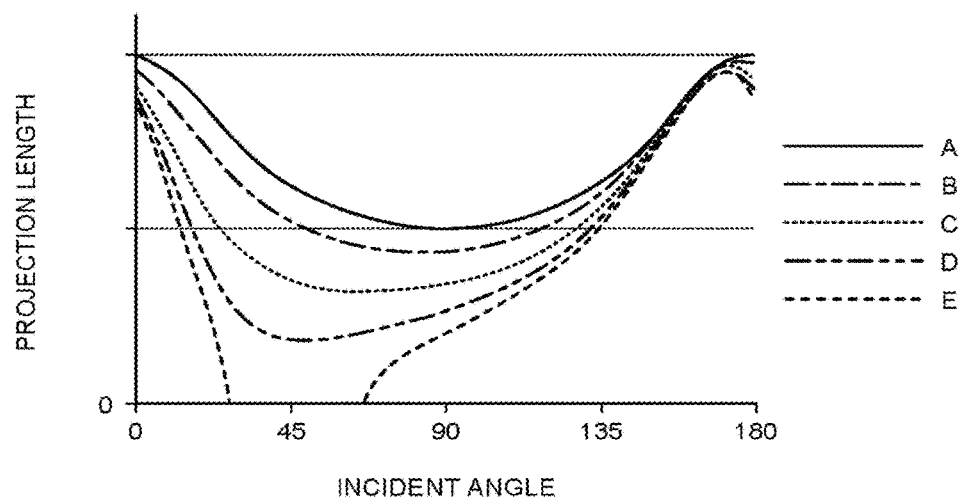
FIG. 4 is a schematic illustrating a relation between an incident angle and a projection length of X-rays to each of the point A, the point B, the point C, the point D, and the point E illustrated in FIG. 3.

FIG. 4 is a schematic illustrating a relation between an incident angle and a projection length of X-rays to each of the point A, the point B, the point C, the point D, and the point E illustrated in FIG. 3. In the following explanation, it is assumed that the X-rays penetrating to each of these five points pass through a plane extending in parallel with the XY plane. The incident angle of the X-rays penetrating to these points is defined by an angle θ measured from a half line extending from the point A in the +X direction.

The behavior of the projection length of the X-rays to the point A with respect to the incident angle exhibits a curve that protrudes downwardly, and is symmetric with respect to the point at an incident angle of 90 degrees, as illustrated in FIG. 4. The projection length of the X-rays to the point A takes its maximum value when the incident angle is 0 degrees and 180 degrees, and takes its minimum value when the incident angle is 90 degrees, as illustrated in FIG. 4. The maximum projection length of the X-rays to the point A is equal to the length of the long axis of the bottom surface of the subject P1. The minimum projection length of the X-rays to the point A is equal to the length of the short axis of the bottom surface of the subject P1. This is because the point A is positioned on the central axis of the subject P1.

Figure 5:
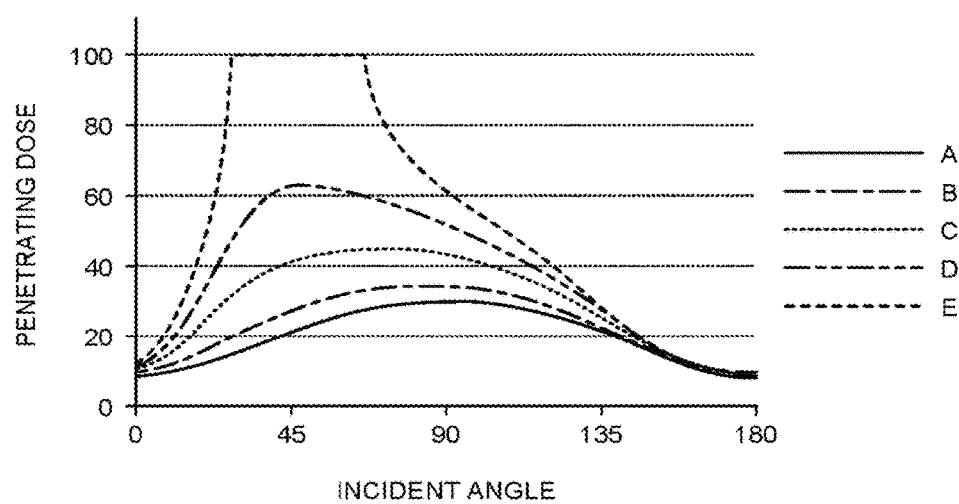
FIG. 5 is a schematic illustrating a relation between an incident angle and a transit dose of the X-rays penetrating to each of the point A, the point B, the point C, the point D, and the point E illustrated in FIG. 3.

FIG. 5 is a schematic illustrating a relation between an incident angle and a transit dose of the X-rays penetrating to each of the point A, the point B, the point C, the point D, and the point E illustrated in FIG. 3. In FIG. 5, 100 represents the X-ray dose with a zero projection length through the subject P1. The behavior of the dose of the X-rays penetrating to each of the point A, the point 2, the point C, the point D, and the point E illustrated in FIG. 3 with respect to the incident angle is as illustrated in FIG. 5, and delineates a curve that is reversal of the curve illustrated in FIG. 4 in the vertical direction. This is because the linear attenuation coefficient for the subject 31 is uniform.

The behavior of the projection length of the X-rays to the point B, the point C, or the point D with respect to the incident angle is as illustrated in FIG. 4, and delineates a curve protruding downwardly. The maximum projection length of the X-rays to the point B, the point C, or the point D is shorter than the length of the long axis of the bottom surface of the subject P1. The maximum projection length of the X-rays to the point B, the point C, or the point D is shorter than the length of the short axis of the bottom surface of the subject P1. The minimum projection length of the X-rays to the point C is shorter than the minimum projection length of the X-rays to the point B, and is larger than the minimum projection length of the X-rays to the point D. The incident angle resulting in the minimum projection length of the X-rays to the point C is smaller than the incident angle at which the projection length of th X-rays to the point B is minimized, and is larger than the incident angle at which the projection length of the X-rays to the point D is maximized. This is because the point B, the point C, and the point D are positioned in the second quadrant of the KY coordinates with their center at the point at the central axis of the subject P1, and the point C is nearer to the surface of the subject P1 than the point B, and further from the surface of the subject P1 than the point D.

The behavior of the projection length the X-rays to the point E with respect to the incident angle includes a part monotonically decreasing, a part staying constant at zero, and a part monotonically increasing, as illustrated in FIG. 4. An incident angle of transmission distance of X-rays passing through the point E is zero is smaller than 90 degrees. This is because the point E is positioned in the second quadrant of the KY coordinates with their center at the point at the central axis of the subject P1, and positioned in an area outside the subject P1.

In the manner described above, the dose of X-rays penetrating to a point of the subject P1 and becoming incident on the detection elements varies depending on the incident angle, even when the point remains the same. Therefore, the effect of the pulse pile-up on the X-ray photon count counted by the photon counting function 161 differs depending on the incident angle of the X-rays, eves at the same point of the subject P1.

The processing circuitry 36 corrects the photos-counting projection data based on the transit dose calculated at Step S5 (Step S6). An example of the process at Step S6 is as described below.

The processing circuitry 36 reads a computer program corresponding to the correcting function 364 from the memory circuitry 35 and executes the computer program. The correcting function 364 corrects the X-ray photon count counted by the photon counting function 161, counted for each energy bin set in the X-ray energy distribution, for each position of the X-ray tube 141, and for each of the detection elements, based on the calculated dose. In other words, the correcting function 364 corrects the X-ray photon count counted by the photon counting function 161 to the count assuming that the X-ray photon count counted by the photon counting function 161 is proportional to the X-ray photon count being incident on the detection elements. The correcting function 364 uses the relation illustrated in FIG. 6 to perform this correction.

Figure 6:
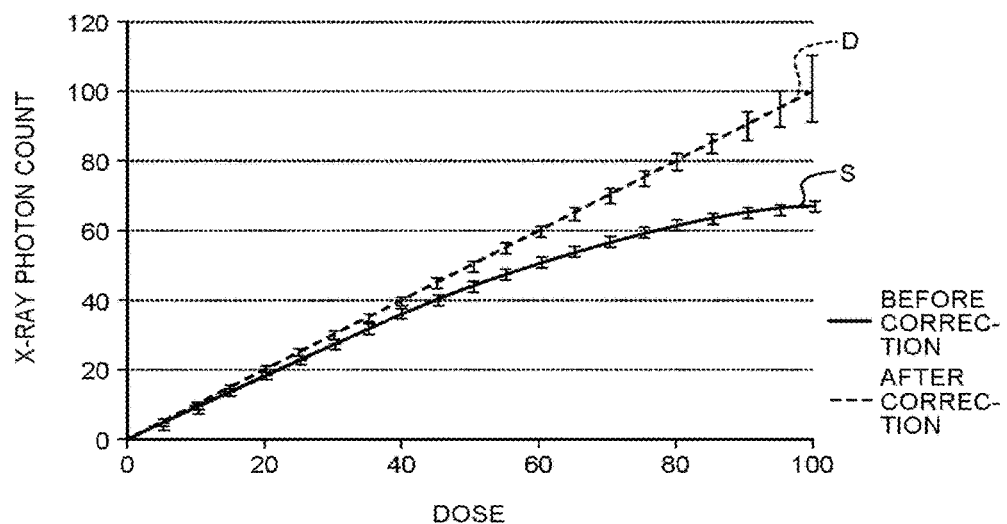
FIG. 6 is a schematic illustrating a relation between an X-ray dose of and the photon count of the X-rays incident on a detection element.

FIG. 6 is a schematic illustrating a relation between the X-ray dose and the photon count of the X-rays incident on the detection element. The dotted line D illustrated in FIG. 6 represents a relation assuming that the X-ray photon count counted by the photon counting function 161 is proportional to the X-ray dose incident on the detection element. The solid line S illustrated in FIG. 6 represents the behavior of the X-ray photon count counted by the photon counting function 161 with respect to the X-ray dose incident on the detection element. In other words, the solid line S represents the detection characteristics of the detection element. As illustrated in FIG. 6, as the X-ray dose incident on the detection elements increases, the difference between the X-ray photon count represented by the dotted line D and the X-ray photon count represented by the solid line S increases. This is because the pulse pile-up occurs more easily with a larger X-ray dose.

The correcting function 364 corrects the X-ray photon count represented by the dotted line D by multiplying the X-ray photon count represented by the solid line S by a predetermined constant, at each dose. The predetermined constant varies depending on the dose. In other words, the solid line S represents the behavior of the X-ray photon count with respect to the X-ray dose before the correction. The dotted line D represents the behavior of the X-ray photon count with respect to the X-ray dose after the correction.

The error bars on the solid line S represent errors in the X-ray photon counts counted by the photon counting function 161 at the respective doses. Each of these errors covers a range of twice the standard deviation of the corresponding X-ray photon count counted by the photon counting function 161 at each dose, for example. The error bars on the dotted line D represent errors in the X-ray photon count corrected by the correcting function 364 at the respective doses. Each of these errors represents a range resultant of multiplying the corresponding error in the X-ray photon count counted by the photon counting function 161 by a predetermined constant, at the corresponding dose, for example. As the X-ray dose incident on the detection element increases, the error in the X-ray photon count corrected by the correcting function 364 increases at the corresponding dose, as illustrated in FIG. 6. These errors described above may be calculated based on the Poison distribution of the photon counts of the X-rays incident on the detection element.

The processing circuitry 36 then applies the pre-process to the corrected photon-counting projection data as illustrated in FIG. 2 (Step S7). The processing circuitry 36 reads a computer program corresponding to the pre-processing function 362 from the memory circuitry 35 and executes the computer program, in the same manner as at Step S3. The pre-processing function 362 applies a correcting to the photon-counting projection data, in the same manner as at Step S3. The photon-counting projection data corrected by the pre-processing function 362 is stored in the projection data memory circuitry 33. The photon-counting projection data corrected by the pre-processing function 362 is also referred to as raw data.

The processing circuitry 6 reconstructs the photon-counting projection data applied with the pre-process, and generates a substance decomposing image, as illustrated in FIG. 2 (Step S8). The processing circuitry 36 reads a computer program corresponding to the image generating function 363 from the memory circuitry 35 and executes the computer program in the same manner as at Step S4. The image generating function 63 includes a function for reconstructing the photon-counting projection data stored in the projection data memory circuitry 33, and generating a substance decomposing image. The reconstruction method is as described at Step S4. The substance decomposing image generated by the image generating function 363 is stored in the image memory circuitry 34. The image generating function 363 may generate at least one of the substance decomposing image, the electron density image, the effective atomic number image, and the monochromatic X-ray image.

The processing circuitry 36 calculates the reliability based on the result of the correcting performed at Step S6, as illustrated in FIG. 2 (Step S9). An example of the process at Step S9 is as described below.

The processing circuitry 36 reads a computer program corresponding to the calculating function 365 from the memory circuitry 35 and executes the computer program. The calculating function 365 is a function for calculating the reliability of pixels in the reconstruction image based on the result corrected by the correcting function 364. The calculating function 365 calculates the reliability in the manner described below, for example.

Figure 7:
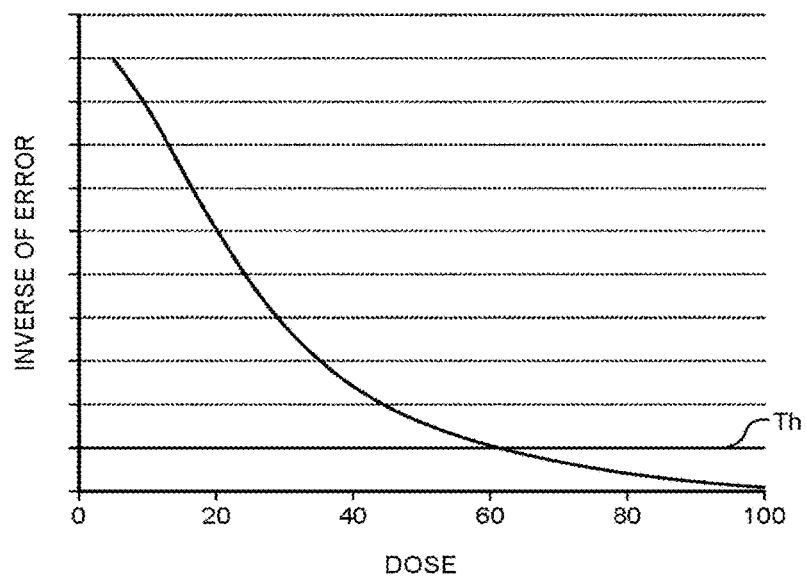
FIG. 7 is a schematic illustrating a relation between an X-ray dose incident on the detection element and the inverse of errors occurring when a correcting function corrects the X-ray photon count.

FIG. 7 is a schematic illustrating a relation between the X-ray dose incident on the detection element and the inverse of errors occurring when the correcting function corrects the X-ray photon count. The threshold Th illustrated in FIG. 7 is used for determining whether the X-ray photon count corrected by the correcting function 364 is reliable. The threshold Th is established by the calculating function 365, for example. When the inverse of errors exceeds the threshold Th, the X-ray photon count corrected by the correcting function 364 is determined to be reliable. When the inverse of errors is equal or smaller than the threshold Th, the X-ray photon count corrected by the correcting function 364 is determined not to be reliable.

When the X-ray dose incident on the detection element is within the range from 0 to 60, the inverse of errors exceeds the threshold Th, as illustrated in FIG. 7. Therefore, when the X-ray dose incident on the detection element is within the range from 0 to 60, the X-ray photon count corrected by the correcting function 364 is determined to be reliable. When the X-ray dose incident on the detection element is within the range from 60 to 100, the inverse of errors is equal or smaller than the threshold Th, as illustrated in FIG. 7. Therefore, when the X-ray dose incident on the detection element is within the range from 60 to 100, the X-ray photon count corrected by the correcting function 364 is determined not to be reliable.

The calculating function 365 calculates lie reliability based on errors occurring when the correcting function 364 corrects the photon count of the X-rays penetrating to the corresponding point of the subject P1. The calculating function 365 calculates, for each point of the subject P1, the quotient of dividing the range of angles in which the inverse of errors occurring when the correcting function 364 corrects the photon count of the X-rays penetrating to such a point exceeds the predetermined threshold, by the entire angle range, as reliability, for example.

To begin with, the calculating function 365 identifies, for each point of the subject P1, a range of angles in which the inverse of errors resultant of correcting the photon count of the X-rays penetrating to the point exceed the threshold Th. In other words, the calculating function 365 identifies, for each point of the subject P1, a range of angles in which the resultant dose of the X-rays penetrating to the point is within the range from 0 to 60. The calculating function 365 then calculates the quotient of dividing the angle range resulting in the dose within the range from 0 to 60 by the entire angle range, as reliability. When there is a plurality of angle ranges resulting in a dose within the range from 0 to 60, the calculating function 365 calculates th quotient of dividing the sum of the angle ranges by the entire angle range, as reliability. When the scan control function 361 performs the full scan, the entire angle range will be 360 degrees. When the scan control function 361 performs half scan, the entire angle range will be 180 degrees.

The processing circuitry 36 displays the morphological image, the substance decomposing image, and the reliability, as illustrated in FIG. 2 (Step S10). An example of the process at Step S10 is as described below.

The processing circuitry 36 reads a computer program corresponding to the display control function 366 from the memory circuitry 35 and executes the computer program. The display control function 366 is a function for displaying the reconstruction image, the reliability, and the like, on the display 32.

Figure 8:
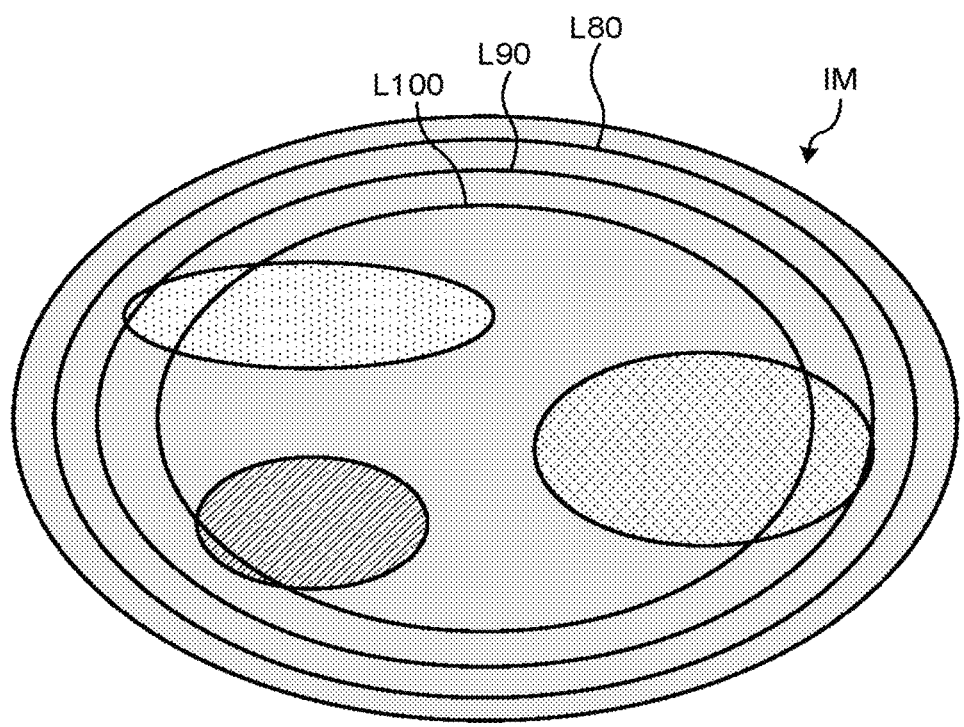
FIG. 8 is a schematic illustrating exemplary reliabilities displayed with a morphological image of a subject.

The display control function 366 displays the reliability, together with the reconstruction image, as illustrated in FIG. 8, for example. Specifically, for example, the display control function 366 displays the reliabilities as closed curves L80, L90, and L100, on the display 32. The closed curve L80 represents that the reliability of the luminance at the pixels of the area surrounded by the closed curve L80 is equal to or greater than 80. The closed curve L90 represents that the reliability of the luminance at each of the pixels inside the area surrounded by the closed curve L90 is equal to or greater than 90. The closed curve L100 represents that the reliability of the luminance at each of the pixels inside the area surrounded by the closed curve L100 is 100.

The display control function 366 displays the reliabilities in a manner superimposed on a substance decomposing image IM, as illustrated in FIG. 8. Specifically, the display control function 366 displays the closed curves L80, L90, and L100 indicating the respective reliabilities in a manner superimposed on the substance decomposing image IM. Alternatively, the display control function 366 may display the reliabilities when the cursor being displayed is moved, for example. Specifically, the display control function 366 may display the closed curves L80, L90, and L100 indicating the respective reliabilities when the cursor being displayed is moved. The display control function 366 may display the reliabilities in a manner superimposed on an electron density image, an effective atomic number image, or a monochromatic X-ray image, instead of the substance decomposing image IM.

The photon-counting X-ray CT apparatus 1 according to the embodiment is as described above. The processing circuitry 36 causes the correcting function 364 to correct the X-ray photon count counted by the photon counting function 161 based on the detection characteristics of the detection element, causes the calculating function 365 to calculate the reliability of a pixel in the reconstruction image based on the result corrected by the correcting function 364, and causes the display 32 to display the reliability. Therefore, the photon-counting X-ray CT apparatus 1 can provide a reconstruction image facilitating a radiologist to make a correct diagnosis.

As explained with reference to FIGS. 3, 4, and 5, as the point through which the X-rays pass is nearer to the surface of the subject, the projection length of the X-rays through the subject decreases, whereas the X-ray dose incident on the detection element increases. This phenomenon is more prominent in the photon-counting X-ray CT apparatus 1, because the photon-counting X-ray CT apparatus 1 irradiates the subject with X-rays from different directions to collect projection data. Therefore, the effect described above is important for the photon-counting X-ray CT apparatus 1.

Even when the luminance at a pixel in the photon-counting projection data represents an attenuation coefficient or a projection length calculated by the converting function 164, th calculating function 3 calculates the reliability using the same process as that when a photon count is corrected.

It is also possible for the photon-counting X-ray CT apparatus 1 not to measure the X-ray dose. In other words, the detection element can omit the integration detecting circuitry. In such a case, the data collecting circuitry 16 reads a computer program corresponding to the dose measuring function 162 from the memory circuitry 35 and executes the computer program. The dose measuring function 162 then calculates the X-ray dose incident on the detection element by calculating an energy-integral of the X-ray photon counts counted by the photon counting function 161, for example.

When the statistic serving as an index of the scale of the reliability of a pixel included in the region of interest in reconstruction image is smaller than a predetermined threshold, the scan control function 361 may scan the subject P by causing the X-ray tube 141 to output X-rays resulting in a smaller dose than that of the X-rays having previously output. In this process, the statistic serving as an index of the scale of the reliability does not mean a statistic representing the spread of the reliability such as a standard deviation or a variance, but means a statistic representing the scale of the reliability, such as a minimum value, a maximum value, a median, or an average. The region of interest may be set as the entire reconstruction image.

When the statistic serving as an index of the scale of the reliability of a pixel included in the region of interest in the reconstruction image generated from the projection data collected using the X-rays resulting the dose of 80 illustrated in FIG. 6, for example, is smaller than the predetermined threshold, th scan control function 361 may cause the X-ray tube 141 to output X-rays resulting in the dose of 40 illustrated in FIG. 6 to scan the subject P. Through this operation, the photon-counting X-ray CT apparatus I can generate a reconstruction image representing the region of interest accurately.

In such a case, the scan control function 361 will reduce the X-ray dose to a level where a statistical fluctuation occurs, for the following reason. If the X-ray dose incident on the detection element is extremely low, the electric charge output from the detection element to the photon-counting detecting circuitry and to the integration detecting circuitry will also be extremely small, whereby the projection data generating function 163 will be incapable of generating projection data with a high signal-noise ratio.

The correcting function 364 can perform the process at Step 55 when the X-rays penetrating to each point of the subject pass through a plane intersecting with the XY plane. In this case as well, the correcting function 364 calculates the distance between the two points at which the X-ray intersects with the surface of the subject as a projection length. In this case as well, the projection length is dependent on the X-ray incident angle.

The calculating function 365 may calculate a value to be used in diagnosis, and may map the value to the reliability. The calculating function 365 calculates the coordinates or the volume representing the range to be applied with radiation therapy, for example, by applying a computer-aided diagnosis (CAD) to the reconstruction image. The calculating function 365 then maps the reliability to the coordinates or the volume representing the range to be applied with the radiation therapy. The display control function 366 may display the reliability mapped to the coordinates or the volume representing the range to be applied with the radiation therapy, together with the coordinates or the volume, on the display 32. The way in which the reliability is displayed is not limited to a particular way. Alternatively, the display control function 366 may also display an error in the coordinates or the volume representing the range to be applied with the radiation therapy, calculated based on the mapped reliability. In such a case, the way in which the error is displayed is not limited to a particular way.

The calculating function 365 may also calculate a stenosis rate of a blood vessel based on a substance decomposing image of calcium. The calculating function then maps the stenosis rate to the reliability. The display control function 366 may then display the reliability mapped to the stenosis rate on the display 32, together with the stenosis rate. The way in which the reliability is displayed is not limited to a particular example. The display control function 366 may then display an error of the stenosis rate calculated based on the reliability mapped to the stenosis rate. In such a case, the way in which the error is limited is not limited to a particular example.

The reliability serves as an index of the reliability of the value used in the diagnosis. Therefore, the reliability can serve as information used in making a diagnosis that is made using such a value. The reliability serves as information for enabling a radiation therapy plan to be created, for example.

When an appropriate radiation therapy plan is dependent on the coordinates and the volume of the range to be applied with the radiation therapy, the physician considers the range to be applied with the radiation therapy and the reliability of the range before changing the radiation therapy plan. For example, when there a substance that can attenuate the radiation used in t radiation therapy between the surface of the subject and the range to be applied with the radiation therapy, the physician considers the range to be applied with the radiation therapy and the reliability of the range, and changes the region through which the radiation passes. The physician may also exclude a range having a reliability lower than the predetermined threshold from the range to be applied with the radiation therapy. In such a case, the display control function 366 may display an image indicating that there is some area having a reliability lower than the predetermined threshold within the range to be applied with the radiation therapy, on the display 32. The physician may also use an electron density image to create a radiation therapy plan. In such a case, the physician creates a radiation therapy plan, considering the radiation range or the dose distribution in the subject P, which are calculated based on the electron density by the calculating function 365, and the reliability mapped to the radiation range or to the dose distribution.

The calculating function 365 may calculate any value other than those described at Step S9 as reliability. The calculating function 365 may calculate any of the following values as reliability, for example. Used in the following is an example in which the inverse of errors behaves with respect to the X-ray dose incident on the detection elements in the manner illustrated in FIG. 7, and the threshold Th is established as illustrated in FIG. 7.

The calculating function 365 calculates, for each point of the subject P, the quotient of dividing the angle range in which the inverse of errors occurring when the correcting function 364 corrects the photon count of th X-rays penetrating to the point exceeds the predetermined threshold, by the range of angle in which the same inverse of errors is equal or smaller than the predetermined threshold, as reliability.

To begin with, the calculating function 365 identifies, for each point of the subject P, a range of angles in which the inverse of errors resultant of correcting the photon count of the X-rays penetrating to the point exceeds the threshold Th. In other words, the calculating function 365 identifies, for each point of the subject P, a range of angles in which the resultant dose of the X-rays penetrating to the point is within the range from 0 to 60. The calculating function 365 then identifies, for each point of the subject, a range of angles in which the inverse of errors occurring in correcting the photon count of the X-rays penetrating to the point is equal or smaller than the threshold Th P. In other words, th calculating function 365 identifies, for each point of the subject P, a range of angles in which the resultant dose of the X-rays penetrating to the point is within the range from 60 to 100.

The calculating function 365 then calculates the quotient of dividing the angle range resulting in a dose within the range from 0 to 60 by the angle range resulting in a dose within a range from 60 to 100, as reliability. When there is a plurality of angle ranges resulting in a hose within the range from 0 to 60, the calculating function 365 calculates the reliability using the sum of such angle ranges. When there is a plurality of angle ranges resulting in a dose within the range from 60 to 100, the calculating function 365 calculates the reliability using the sum of such angle ranges.

Alternatively, the calculating function 365 may calculate the reliability of a pixel by calculating, for each point of the subject P, an integral of the inverse of errors occurring when the correcting function 364 corrects the photon count of the X-rays penetrating to the point, over a range of the X-ray incident angle. For example, the calculating function 365 calculates, for each point of the subject P, an integral of the inverse of errors occurring when the correcting function 364 corrects the photon count of the X-rays penetrating to the point, over the range of angles in which such an inverse of errors exceeds the predetermined threshold, and then calculates the quotient of dividing such an integral by an integral of the same inverse of errors over the entire angle range, as reliability.

To begin with, the calculating function 365 Identifies, for each point of th subject P, a range of angles in which the inverse of errors resultant of correcting the photon count of the X-rays penetrating to the point exceeds the threshold Th. In other words, the calculating function 365 identifies, t for each point the subject P, a range of angles in which the resultant dose of the X-rays penetrating to the point is within the range from 0 to 60. The calculating function 365 then calculates an integral of the inverse of errors over the angle range resulting in a dose within the range from 0 to 60, and then calculates the quotient of dividing such an integral by an integral of the inverse of errors over the entire angle range, as reliability.

Alternatively, the calculating function 365 may calculate the reliability of a pixel by calculating, for each point of the subject P, an integral of the inverse of errors occurring when the correcting function 364 corrects the photon count f the X-rays penetrating to the point, over a range of the X-ray incident angle. For example, the calculating function 365 calculates, for each point of the subject 6, an integral of the inverse of errors occurring when the correcting function 364 corrects th photon count of the X-ray penetrating to the point, over th range of angles in which the inverse of errors exceeds the predetermined threshold, and calculates the quotient of dividing such an integral by an integral of the inverse of errors over a range of angles in which the inverse of errors is equal or smaller than the predetermined threshold, as reliability.

To begin with, the calculating function 365 identifies, for each point of the subject P, a range of angles in which the inverse of errors resultant of correcting the photon count of the X-rays penetrating to th point exceeds the threshold Th. In other words, the calculating function 365 identifies, for each point of the subject P, a range of angles in which the resultant dose of the X-rays penetrating to the point is within the range from 0 to 60. The calculating function 365 then identifies, for each point of the subject P, a range of angles in which the inverse of errors resultant of correcting the photon count of the X-rays penetrating to the point is equal or smaller than the threshold Th. In other words, the calculating function 365 identifies, for each point of the subject P, a range of angles in which the resultant dose of the X-rays penetrating to the point is within the range from 60 to 100.

The calculating function 365 then calculates the quotient of dividing the integral of the inverse of errors over the angle range resulting in a dose within the range from 0 to 60, by the integral of the inverse of errors over the angle range resulting in a dose within a range from 60 to 100, as reliability. When there is a plurality of angle ranges resulting in a dose within the range from 0 to 60, the calculating function 365 calculates the reliability using the sum of such angle ranges. When there is a plurality of angle ranges resulting in a dose within a range from 60 to 100, the calculating function 365 calculates the reliability using the sum of such angle ranges.

Alternatively, the calculating function 365 calculates, for each point of the subject P, the quotient of dividing the range of angles in which the difference between the X-ray photon count assuming that the X-ray photon count counted by the photon counting function 161 is proportional to the X-ray photon count incident on the detection element, and the K-ray photon count counted by the photon counting function 161 exceeds the predetermined threshold, by the entire angle range, as reliability.

The calculating function 365 identifies, for each point of the subject P, a range of angles in which the difference between the X-ray photon count of the X-rays penetrating to the point, indicated by the dotted line D in FIG. 6, and the X-ray photon count indicated by the solid line S in FIG. 6 exceeds the predetermined threshold. This predetermined threshold is used for determining whether the X-ray photon count corrected by the correcting function 364 is reliable. This predetermined threshold is established by the calculating function 365, for example. If this difference is smaller than the predetermined threshold, the X-ray photon count corrected by the correcting function 364 is determined to be reliable. If this difference is equal to or greater than the predetermined threshold, the X-ray photon count corrected by the correcting function 364 is determined not to be reliable. The calculating function 365 then calculates the reliability described above.

Alternatively, the calculating function 365 may calculate, for each point of the subject P, the quotient of dividing the range of angles in which the difference between the photon count assuming that the X-ray photon count counted by the photon counting function 161 is proportional to the X-ray photon count incident on the detection element and the X-ray photon count counted by the photon counting function 161 is smaller than the predetermined threshold, by the range of angles in which such a difference is equal to or greater than the predetermined threshold, as reliability.

Alternatively, the calculating function 365 calculates, for each point of the subject P, an integral of the difference between the photon count assuming that the X-ray photon count counted by the photon counting function 161 is proportional to the X-ray photon count incident on the detection element, and the X-ray photon count counted by the photon counting function 161, over the range of angles in which such a difference is smaller than the predetermined threshold, and calculates the quotient of dividing the integral by an integral of the difference over the entire angle range, as reliability.

To begin with, the calculating function 365 identifies, for each point of the subject P, a range of angles in which the difference between the X-ray photon count of the X-rays penetrating to the point indicated by the dotted line D in FIG. 6 and the X-ray photon count indicated by the solid line S in FIG. 6 exceeds the predetermined threshold. The calculating function 365 calculates the reliability described above.

Alternatively, the calculating function 365 calculates, for each point of the subject F, an integral of the difference between the photon count assuming that the X-ray photon count counted by the photon counting function 161 is proportional to the X-ray photon count incident on the detection element and the X-ray photon count counted by the photon counting function 161, over the range of angles in which the difference is smaller than the predetermined threshold, and calculates the quotient of dividing the integral by an integral of the difference over the range of angles in which the difference is equal to or greater than the predetermined threshold, as the reliability.

Even when the reliability described above is calculated, instead of the reliability calculated by the calculating function 365 at Step 59, the photon-counting X-ray CT apparatus 1 can also achieve the advantageous effects described above.

Examples of the processor described above include a central processing unit (CPU), a graphics processing unit (CPU), an application specific integrated circuit (ASIC), a programmable logic, device (PLD), and a field programmable gate array (FPGA). Examples of the programmable logic device (PLD) include a simple programmable logic device (SPLD) and a complex programmable logic device (CPLD).

In the embodiment described above, the high voltage generating circuitry 11, the collimator adjusting circuitry 12, the gantry driving circuitry 13, the data collecting circuitry 16, the couch driving circuitry 22, and the processing circuitry 36 are implemented by reading a computer program stored in the memory circuitry 35 and executing the computer program, but embodiments are not limited thereto. Instead of storing the computer program in the memory circuitry 35, a computer program may be embedded in each of these pieces of circuitry. These pieces of circuitry then implement the functions by reading the directly embedded computer program and executing the computer program.

Each of the circuitry illustrated in FIG. 1 may be distributed or integrated as appropriate. For example, the processing circuitry 36 may be distributed to scan control circuitry, pre-process circuitry, image generating circuitry, correcting circuitry, calculating circuitry, display control circuitry, and control circuitry executing the functions of the scan control function 361, the pre-processing function 362, the image generating function 363, the correcting function 364, the calculating function 365, the display control function 366, and the control the function 367, respectively. The data collecting circuitry 16 may be distributed to photon counting circuitry, dose measuring circuitry, projection data generating circuitry, and conversion circuitry that implement the functions of the photon counting function 161, the dose measuring function 162, the projection data generating function 163, and the converting function 164, respectively. Furthermore, the high voltage generating circuitry 11, the collimator adjusting circuitry 12, the gantry driving circuitry 13, the data collecting circuitry 16, the couch driving circuitry 22, and the processing circuitry 36 may be integrated in any way.

The processes other than that at Step S1 may be executed by an image processing apparatus, instead of the photon-counting X-ray CT apparatus 1. Such an image processing apparatus has a correcting function and a calculating function. The correcting function corrects the X-ray photon count counted for each energy bin set in the energy distribution of the X-rays output from the X-ray tube 141, for each position of the X-ray tube 141, and for each detection element detecting the incident X-ray photons, based on the detection characteristics of the detection element. The calculating function calculates the reliability of a pixel in the reconstruction image, based on the result corrected by the correcting function.

According to at least one of the embodiments described above, diagnoses using reconstruction images can be performed appropriately.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such for modifications as would fall within the scope and spirit of the inventions.

What is claimed is:

1. A photon-counting X-ray computed tomography (CT) apparatus, comprising:
    an X-ray tube that irradiates a subject with X-rays;
    a detector including a plurality of detection elements configured to detect photons of the X-rays incident on the detection elements;
    photon counting circuitry configured to count a count of X-ray photons for each energy bin set in an energy distribution of the X-rays, for each position of the X-ray tube, and for each of the detection elements;
    correcting circuitry configured to correct the count of the X ray photons counted by the photon counting circuitry, based on a detection characteristic of the detection elements;
    calculating circuitry configured to calculate as reliability of a pixel in a reconstruction image based on the correction; and
    conversion circuitry configured to calculate an attenuation coefficient of the X-rays penetrating through the subject, based on the count of the X-ray photons counted by the photon counting circuitry, wherein
    the correcting circuitry is further configured to correct the attenuation coefficient calculated by the conversion circuitry.

2. The photon-counting X-ray CT apparatus according to claim 1, Wherein the correcting circuitry is further configured to correct the count of the X-ray photons counted by the photon counting circuitry to a count, under an assumption that the count of the X-ray photons counted by the photon counting circuitry is proportional to a count of X-ray photons incident on the detection elements.

3. The photon-counting X-ray CT apparatus according to claim 1, wherein the calculating circuitry is further configured to calculate a value used in a diagnosis, and to map the value to the reliability.

4. The photon-counting X-ray CT apparatus according to, claim 1, further comprising a display configured to display the reliability.

5. The photon-counting X-ray CT apparatus according to claim 4, wherein the display is configured to display the reliability, together with the reconstruction image.

6. The photon-counting X-ray CT apparatus according to claim 5, wherein the display is configured to display the reliability in a manner superimposed on the reconstruction image.

7. The photon-counting X-ray CT apparatus according to claim 5, wherein the display is configured to display the reliability when a cursor being displayed is moved.

8. The photon-counting X-ray CT apparatus according to claim 1, further comprising scan control circling configured, when a statistic of a pixel included in a region of interest in the reconstruction image and serving as an index of scale of the reliability is smaller than a predetermined threshold, to cause the X-ray tube to output X-rays at a dose lower than the X-rays, and to scan the subject.

9. A photon-counting X-ray computed tomography (CT) apparatus, comprising:
an X-ray tube that irradiates a subject with X-rays;
a detector including a plurality of detection elements configured to detect photons of the X-rays incident on the detection elements;
photon counting circuitry configured to count a count of X-ray photons for each energy bin set in an energy distribution of the X-rays, for each position of the X-ray tube, and for each of the detection elements:
correcting circuitry configured to correct the count of the X-ray photons counted by the photon counting circuitry, based on a detection characteristic of the detection elements;
calculating circuitry configured to calculate reliability of a pixel in a reconstruction image based on the correction; and
conversion circuitry configured to calculate an X-ray protection length through the subject, based on the count of the X-ray photons counted by the photon counting circuitry, wherein
the correcting circuitry is further configured to correct the projection length calculate by the conversion circuitry.

10. An image processing apparatus, comprising:
correcting circuitry configured to correct a count of X-ray photons counted for each energy bin set in an energy distribution of X-rays output from an X-ray tube, for each position of the X-ray tube, and for each detection element detecting photons of X-rays incident on the detection element, based on a detection characteristic of the detection elements;
calculating circuitry configured to calculate a reliability of a pixel in a reconstruction image based on a result corrected by the correcting circuitry; and
conversion circuitry configured to calculate an attenuation coefficient of the X-rays penetrating through the subject, based on the count of the X-ray photons counted by the photon counting circuitry, wherein
the correcting circuitry is further configured to correct the attenuation coefficient calculated by the conversion circuitry.

* * * * *